(12) United States Patent
Khachin et al.

(10) Patent No.: US 7,640,952 B2
(45) Date of Patent: Jan. 5, 2010

(54) METHOD FOR MANUFACTURING A SURGICAL DEVICE FOR EXTRACTING A FOREIGN OBJECT

(75) Inventors: Vladimir Khachin, Tomsk (RU); Stepan Khachin, Tomsk (RU); Valery Diamant, Katzrin (IL)

(73) Assignee: Lithotech Medical Ltd., Katzrin (IL)

( * ) Notice: Subject to any disclaimer, the term of this patent is extended or adjusted under 35 U.S.C. 154(b) by 852 days.

(21) Appl. No.: 11/159,396

(22) Filed: Jun. 23, 2005

(65) Prior Publication Data

US 2006/0004404 A1    Jan. 5, 2006

Related U.S. Application Data

(63) Continuation-in-part of application No. PCT/IL02/10128, filed on Dec. 23, 2002, and a continuation-in-part of application No. 10/216,672, filed on Aug. 12, 2002, now Pat. No. 7,101,380.

(51) Int. Cl.
*B21F 27/02* (2006.01)
(52) U.S. Cl. .................. 140/17; 606/127; 606/200; 140/5
(58) Field of Classification Search .......... 606/110, 606/113, 114, 127, 128, 106, 200; 140/5, 140/7, 17, 35, 48, 102, 111
See application file for complete search history.

(56) References Cited

U.S. PATENT DOCUMENTS

| | | | |
|---|---|---|---|
| 2,943,626 | A | 7/1960 | Dormia |
| 3,137,298 | A | 6/1964 | Glassman |

(Continued)

FOREIGN PATENT DOCUMENTS

EP    0 820 729 A1    1/1998

(Continued)

OTHER PUBLICATIONS

XP-002172655: Abstract for RU2022528, Sveshnikov, A. et al, "instrument remove Stone Ureter Cage Made Branch Support Cable Enclose Withdraw Stone," Nov. 15, 1994.

*Primary Examiner*—Todd E Manahan
*Assistant Examiner*—Michael G Mendoza
(74) *Attorney, Agent, or Firm*—Browdy and Neimark, PLLC

(57) ABSTRACT

A method for manufacturing the surgical device for removing a foreign object from a body and a retrieval basket of the device are described. The retrieval basket is adapted for entrapping and retaining the object located in the body. The basket comprises a structure having a proximal end and a distal end. The structure is formed by a plurality of filaments fabricated from a single or several wires. The filaments extend from the proximal end towards the distal end, and are bound together to define a plurality of strands. The strands ramify at corresponding branching points into loops having various shapes and sizes. At least a part of the loops are overlapped and/or interlaced so as to define a net, and thereby impart structural rigidity and dilatation ability to the basket when opened. The method of manufacturing the retrieval basket includes selecting at least one wire; weaving the basket from the wire by overlapping and/or interlacing the filaments so that to form a net at least in the vicinity of the distal end; and binding the filaments for forming a shape of the retrieval basket.

32 Claims, 13 Drawing Sheets

U.S. PATENT DOCUMENTS

| | | | |
|---|---|---|---|
| 3,472,230 A | 10/1969 | Fogarty | |
| 3,496,330 A | 2/1970 | Needham | |
| 4,299,225 A | 11/1981 | Glassman | |
| 4,347,846 A | 9/1982 | Dormia | |
| 4,425,908 A | 1/1984 | Simon | |
| 4,590,938 A | 5/1986 | Segura et al. | |
| 4,611,594 A | 9/1986 | Grayhack et al. | |
| 4,619,246 A | 10/1986 | Molgaard-Nielsen et al. | |
| 4,633,871 A | 1/1987 | Shinozuka | |
| 4,790,812 A | 12/1988 | Hawkins, Jr. et al. | |
| 5,057,114 A | 10/1991 | Wittich et al. | |
| 5,064,428 A | 11/1991 | Cope et al. | |
| 5,496,330 A | 3/1996 | Bates et al. | |
| 5,658,296 A | 8/1997 | Bates et al. | |
| 5,792,145 A | 8/1998 | Bates et al. | |
| 6,093,196 A | 7/2000 | Okada | |
| 6,159,220 A | 12/2000 | Gobron et al. | |
| 6,168,603 B1 | 1/2001 | Leslie et al. | |
| 6,171,326 B1 | 1/2001 | Ferrera et al. | |
| 6,183,482 B1 | 2/2001 | Bates et al. | |
| 6,190,394 B1 | 2/2001 | Lind et al. | |
| 6,224,612 B1 | 5/2001 | Bates et al. | |
| 6,302,895 B1 | 10/2001 | Gobron et al. | |
| 6,344,048 B1 | 2/2002 | Chin et al. | |
| 6,348,056 B1 | 2/2002 | Bates et al. | |
| 6,368,328 B1 | 4/2002 | Chu et al. | |
| 6,458,139 B1 | 10/2002 | Palmer et al. | |
| 6,458,145 B1 | 10/2002 | Ravenscroft et al. | |
| 6,511,492 B1 | 1/2003 | Rosenbluth et al. | |
| 6,514,273 B1 | 2/2003 | Voss et al. | |
| 6,569,184 B2 * | 5/2003 | Huter | 606/200 |
| 6,626,915 B2 | 9/2003 | Leveillee | |
| 6,752,811 B2 | 6/2004 | Chu et al. | |

FOREIGN PATENT DOCUMENTS

| | | |
|---|---|---|
| FR | 1.197.808 | 12/1959 |
| RU | 2022528 | 2/1992 |
| SU | 1036325 | 5/1981 |
| WO | WO 92/16153 A1 | 10/1992 |
| WO | WO 96/23446 | 8/1996 |
| WO | WO 01/10290 A2 | 2/2001 |
| WO | WO 02/078632 A2 | 10/2002 |
| WO | WO 03/002006 A1 | 1/2003 |

* cited by examiner

METHOD FOR MANUFACTURING A SURGICAL DEVICE FOR EXTRACTING A FOREIGN OBJECT

CROSS REFERENCE TO RELATED APPLICATIONS

The present application is a continuation-in-part of International Application No. PCT/IL2002/0010128, filed Dec. 23, 2002 and application Ser. No. 10/216,672, filed Aug. 12, 2002 now U.S. Pat. No. 7,101,380. The entire contents of both application being hereby incorporated herein by reference.

FIELD OF THE INVENTION

This invention relates to a fabrication of a medical instrument for removing an object from a body, and in particular, to a fabrication of a surgical device for extracting calculi appearing in the biliary or urinary system.

BACKGROUND OF THE INVENTION

One type of a widely used surgical device is a tool for retrieving foreign material from various sites along the urinary tract of a patient's body. Examples of the foreign material include calculi of different sizes and characteristics.

Referring to FIG. 1, a schematic view, partially in a longitudinal cross-section of the distal end of an example of a conventional surgical retrieval tool is illustrated. The surgical retrieval tool 10 or so-called surgical extractor, generally comprises a flexible tubular catheter 11 formed as a tubular sheath adapted to penetrate the body passages to reach the location where the object (not shown) to be evacuated is located. A manipulation rod or cable 12 is located within the catheter 11, which can be manipulated from the outside at the catheter's proximal end. The rod 12 is coupled to a basket 13 capable to be deployed within the sheath. The basket 13 consists of flexible filaments 14 and, for example, can be made of either stainless steel or any other material capable to provide the basket with elasticity. According to the example shown in FIG. 1, the filaments 14 are bound together in the vicinity of a basket proximal end to form strands 19 as well as at a basket distal end to form a tip 15. The basket 13 is usually connected to the manipulation rod 12 via a sleeve connector 17 bounding the strands and filaments together.

One of the drawbacks of the conventional surgical extractor is associated with the discrepancy of the inner diameter of the catheter 11, the diameter of the manipulating rod 12 and the diameter of the connector 17. Due to this discrepancy, an air gap 18 between the inner wall of the catheter 11 and the rod 12 significantly affects deformation properties of the catheter and the ability of the catheter to bend without destruction on large angles.

Depending on the manipulation, the basket 13 may either retract inside the sheath to allow penetration of the catheter via a passage or protract from the catheter. In the protracted position, the filaments open due to the elasticity of their material and form a cage to thus allow entering the object inside the basket 13 through the open spaces 16 left between its adjacent filaments. Further retraction of the basket inside the sheath results in the cage collapsing and entrapping the object in the basket. Removal of the catheter will enable the whole device to be removed from the body organ together with the object immobilized within the basket.

During an operation, the surgeon moves the catheter behind the object to be extracted, and then protracts the basket from the catheter. Once the basket is protracted it opens (due to its resiliency) and is ready for receiving the object to be entrapped therein. The surgeon pulls the catheter together with the basket until it entraps the object, and thus extracts the entrapped object from the body.

It can be easily appreciated that the particular design of the basket is crucial for entrapping and reliably retaining the object during evacuation. Examples of various types of such retrieval baskets are described in the following documents: U.S. Pat. Nos. 2,943,626; 3,137,298; 3,472,230; 4,299,225; 4,347,846; 4,590,938; 4,633,871; 4,611,594; 4,790,812; 5,057,114; 5,496,330; 5,064,428; 5,658,296; 6,168,603; 6,183,482 and 6,190,394.

It should be noted that generally all conventional retrieval baskets have certain common characteristics. Thus, each retrieval basket comprises a plurality of filaments and can be collapsible into a compact form. The filaments are formed from wires and can be arranged into either multi-filament strands or spaced single filaments.

There are known the baskets that have relatively few widely spaced multi-filament strands at the proximal basket end, for capturing the object. These baskets may include two or more such multi-filament strands between which the objects can pass for entrapping within the retrieval basket. On the other hand, the filaments are closely spaced in the vicinity of the distal basket end, to provide an enclosure for retaining objects captured within such retrieval baskets. In some retrieval baskets the strands are formed along substantially straight lines when the basket is in compact form; in others, the individual strands extend along a generally helical path.

Forming the conventional baskets generally comprises grouping a plurality of axially extending filaments, strips or wires having shape memory or superelastic properties to extend along the basket axis and bounding them together at distal and proximal basket ends between which each of the wires extend.

In order to increase the number of contacts between the basket and entrapped calculi, additional filaments would be advantageous. However, an inner diameter of the catheter imposes an upper limit on the filament number and their diameter. Thus, for sufficient strength of the basket, the basket design involves a compromise between the number of filaments (needed to retain objects and enable the capture of the objects) and the wire diameter.

It can be appreciated that rigid wire materials can be employed in order to enhance the strength of the basket. However, the utilization of rigid materials can result in a decrease in flexibility that is necessary to provide penetration of the basket in body tracts having small diameters, tortuous pathways and irregular lumens.

SUMMARY OF THE INVENTION

Despite the extensive prior art in the area of surgical devices employing retrieval baskets for extracting objects from a body and methods for manufacturing thereof, there is still a need in the art for, and it would be useful to have a convenient and safe surgical device suitable for the reliable and efficient extraction of foreign objects from the body as well as a novel and repeatable method for producing thereof.

It would be advantageous to have a repeatable method for producing a novel surgical device provided with a retrieval basket having enhanced structural rigidity and dilatation ability, thus reducing the probability of traumatizing of adjacent body tissues.

It would also be advantageous to have a repeatable method for producing a novel surgical tool provided with a catheter capable to withstand various bends on relatively large angles, thus enabling more reliable functioning during surgical treatment.

It would yet be advantageous to have a repeatable relatively inexpensive method for producing a retrieval basket from one piece of wire or from several wires.

The present invention satisfies the aforementioned need by providing a method for manufacturing a retrieval basket suitable for entrapping and retaining the object during extraction. The basket comprises a structure having a proximal end and a distal end. The structure is formed by a plurality of filaments fabricated from a single or several wires. The filaments extend between the proximal end and the distal end. At least a part of the filaments, which originate from the proximal end, can arrive at the proximal end after winding. At least a part of the filaments are configured in the form of loops. The filaments, from which the loops are made, can overlap and/or interlace so as to define a net, and thereby to impart structural rigidity and dilatation ability to the basket when it is opened.

Note that the term "overlap" herein is assigned to such arrangement of the filaments, in which one element crosses other filaments, i.e., one of the filaments always being over or under the other filaments. The term "interlace" herein is assigned to the situation when at least one filament interweaves with the other filaments, i.e., one of the filaments passes first above the crossed filament and then passes under the next crossed filament.

According to one embodiment of the basket of the invention, the size of holes (cells) of the net decreases from the proximal end towards the distal end. In other words, the density of the net increases from the proximal end to the distal end of the structure.

According to a further embodiment of the basket, the filaments in a region of the structure at the proximal end form at least two strands, each including a plurality of the filaments. According to this embodiment, the structure of the basket has a parachute-like shape, i.e., a form of the basket is symmetrical along the basket central axis.

According to a still further embodiment of the basket of the invention, the filaments in a region of the structure at the proximal end form a plurality of strands and one of the strands is common for all the filaments. The structure of the basket, according to this embodiment, has a spoon-like shape.

According to a yet further embodiment of the basket of the invention, the filaments are bound together at the distal ends to form a basket tip.

According to a still further embodiment of the basket of the invention, the filaments are bound together at the proximal end to form a manipulation cable.

According to another aspect, the invention relates to a production of a medical device for retrieving an object from a body. The medical device includes the retrieval basket of the present invention, a flexible tubular catheter (designed as a sheath) adapted to penetrate along the body passages near the location of the object, and a manipulator coupled to the retrieval basket via a manipulation cable. The catheter is suitable either for retracting the basket within the sheath, to enable bringing the catheter within the body, or for protracting the basket from the sheath to enable opening of the basket.

According to one embodiment of the medical device of the invention, the manipulation cable is produced as an integral part of the basket. In this case at least a part of the cable is formed from the basket's filaments which are bound together at the basket proximal end and extended towards the manipulator.

According to a further embodiment of the medical device, at least a portion of the manipulation cable is covered by a filling tubing. The outer diameter of the filling tubing has a sufficient magnitude to substantially fill the gap between the inner wall of the catheter and the manipulation cable, in order to enhance the ability of the catheter to bend without destruction on large angles.

According to a still another embodiment of the medical device of the invention, the manipulation cable is produced as a separate unit that is coupled to the manipulator and to the basket. The joint between the cable and the basket is accomplished by means of a bushing. For example, the bushing can be in the form of a pipe made of metal, e.g., Ni, stainless steel, etc.

The present invention also satisfies the aforementioned need by providing a process for manufacturing a retrieval basket suitable for entrapping the object and its retaining during the extraction. The process begins with a step of selection of a predetermined number of wires having a predetermined diameter and length.

According to one non-limiting example of the process, the manufacturing of the retrieval basket is carried out from one piece of wire.

According to another non-limiting example of the process the manufacturing of the retrieval basket is carried out from several wires.

It should be noted that the wires selected for the construction of the basket can be single-filament wires, or when desired, can be multi-filament wires.

Furthermore, the process for fabrication of the retrieval basket includes weaving the retrieval basket. The weaving can be carried out from one piece of wire or from several wires.

According to one embodiment of the invention, at least a part of the weaving of the retrieval basket is performed on a weaving jig having a predetermined pattern formed by grooves configured on the jig's surface.

Thereafter, the process includes forming a shape of the retrieval basket. According to one embodiment of the invention, the forming of a shape includes binding the filaments on a shape-forming jig which for this purpose has a predetermined shape. According to this embodiment, the forming of a shape further includes shape storing annealing the basket mounted on the shape-forming jig.

Such forming a shape allows the basket to impart the structural rigidity and dilatation abilities, when the basket is opened.

The process for fabrication of the retrieval basket can include binding the filaments together at the proximal end to form a manipulation cable.

When required, the process can also include binding the filaments together at the distal end to form a basket tip.

Thus, in accordance with one broad aspect of the invention, there is provided a method for manufacturing a retrieval basket having a proximal end and a distal end and constituted by a plurality of wire filaments extending from the proximal end towards the distal end, comprising:

selecting at least one wire;

weaving the basket from the wire, wherein said weaving includes forming portions from wire filaments that are bound together to define a plurality of strands, said plurality of strands ramify at corresponding branching points into loops having various shapes and sizes, at least a part of the loops are overlapped and/or interlaced so as to define a net at least at the distal end; and forming a shape of the retrieval basket, thereby imparting structural rigidity and dilatation abilities to the basket when opened.

In accordance with another broad aspect of the invention, there is provided a method for manufacturing a surgical device for removing a foreign object from a body, comprising:

providing a retrieval basket fabricated according to claim 1 configured for entrapping and retaining the object located in the body for its extraction therefrom;

providing a basket control assembly comprising a tubular sheath adapted to penetrate into the body for reaching the object, a manipulator for manipulating the basket for extraction the object from the body, and a manipulation cable arranged within the sheath for connecting the basket to the manipulator, where the assembly is configured for retracting the basket within the sheath and protracting the basket therefrom for its opening; and coupling the retrieval basket to the basket control assembly.

There has thus been outlined, rather broadly, the more important features of the invention in order that the detailed description thereof that follows hereinafter may be better understood. Additional details and advantages of the invention will be set forth in the detailed description, and in part will be appreciated from the description, or may be learned by practice of the invention.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF SPECIFIC EMBODIMENTS

Figure 1:
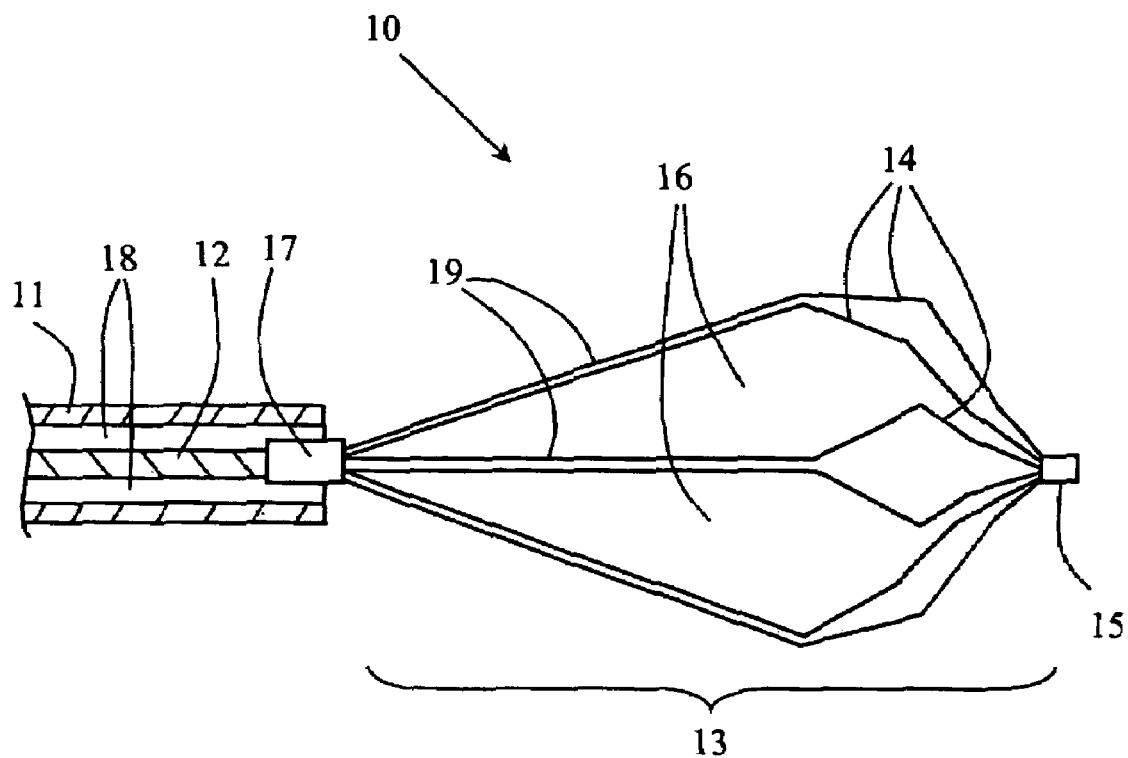
FIG. 1 is a schematic view, partially in a longitudinal cross-section, of the distal end of a conventional surgical extractor.

The principles of the method for surgical device according to the present invention may be better understood with reference to the drawings and the accompanying description, wherein like reference numerals have been used throughout to designate identical elements. It being understood that these drawings are given for illustrative purposes only and are not meant to be limiting.

Referring now to FIG. 2A through FIG. 2D, four non-limiting examples of a retrieval basket 20 shaped in a parachute-like fashion are illustrated, according to the present invention. In general, the basket 20 comprises a structure having a proximal end 21 and a distal end 22. The structure is formed by a plurality of filaments fabricated from a single wire in the manner describe below. The filaments extend between the proximal end 21 and the distal end 22. At least a part of the filaments, which originate from the proximal end 21, can arrive at the proximal end 22 after winding. The filaments are entwined and spatially arranged in such manners that upon protracting from a sheath they can be readily spread out. In the vicinity of the proximal end 21 the filaments form strands 211, 212, 213 and 214. These strands ramify at branching points 215, 216, 217, and 218, into loops with various shapes and sizes.

Figure 2A:
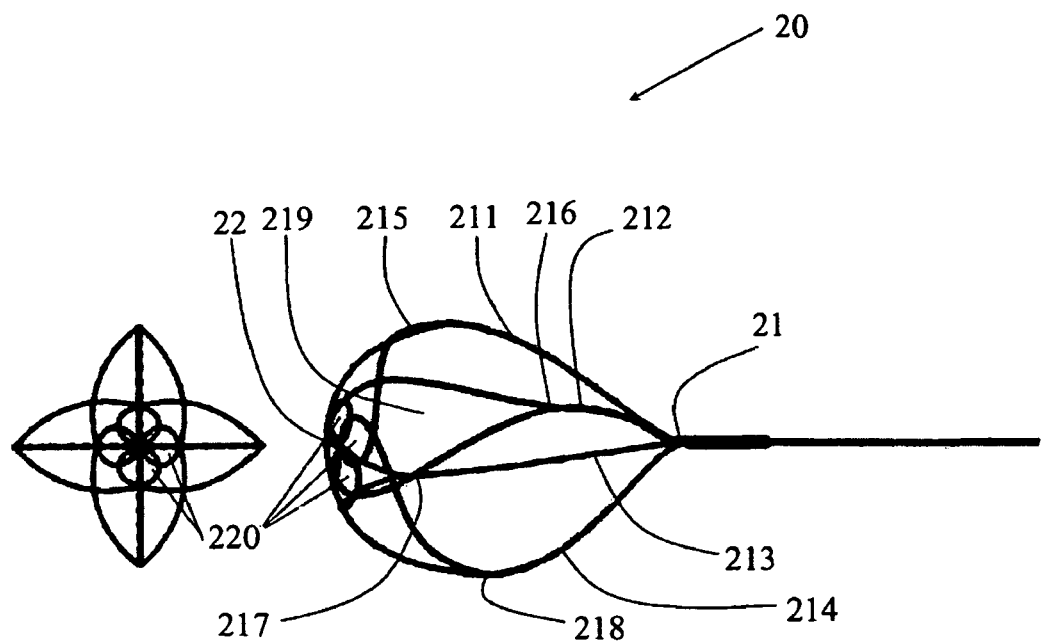
FIG. 2A-FIG. 2E shows a plan and top view of four examples of the retrieval basket manufactured accordance to the present invention.

According to the example shown in FIG. 2A, each strand includes two entwined wire filaments that form loops after the branching point. For instance, after the ramification of the strand 216 the loop 219 emerges from the branching point 216. As can be seen, the loops emerged from the branching points are interlaced so as to define a net at the distal end. Furthermore, the loops are formed in such a manner that additional small loops 220 are arranged at the distal end 22. The loops provided thereby overlap and interlace, thus defining the dense net-like structure of the basket. It should be appreciated that the size of holes (cells) of the net decreases from the proximal end towards the distal end. In other words, the density of the net increases from the proximal end to the distal end of the structure. The increased density of the net allows for entrapment and retention of small objects which would not ordinary be retained in the aforementioned conventional retrieval baskets having the relatively wide spacing (16 in FIG. 1).

It should be appreciated that in contrast to the conventional baskets (e.g., the basket shown in FIG. 1), the filaments of the basket of the present invention are overlapped and interlaced so as to define a net, at least in the vicinity of the distal end. This feature imparts an enhanced structural rigidity and dilatation ability to the basket when it is opened. By providing the loops formed by the filaments with various shapes and sizes it is possible to vary also the size and shape of the cells, formed at the intersection of the loops, thus control the capture and retention abilities of the basket.

Figure 2B:
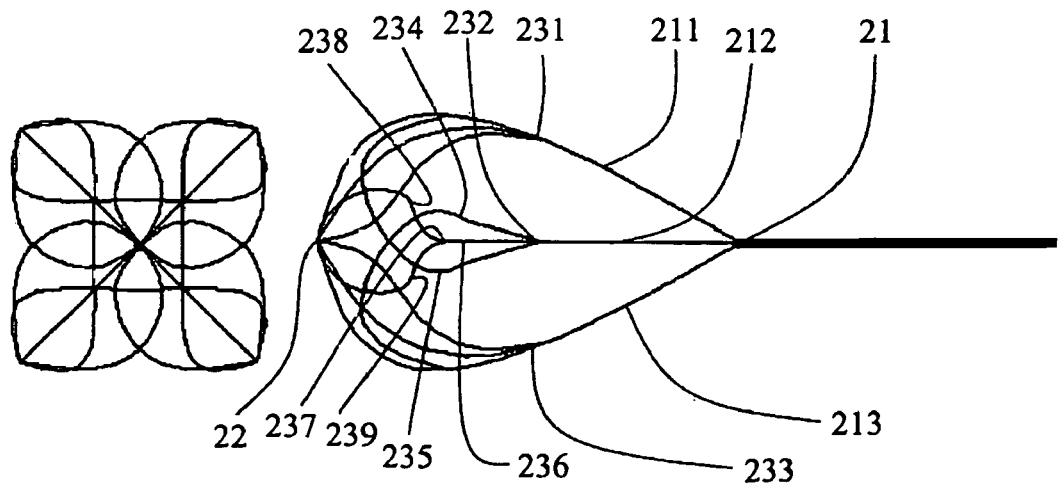

In the example shown in FIG. 2B only three strands 211, 212 and 213 of the retrieval basket 20 can be seen. Each strand is formed of four entwined wire filaments. These strands ramify at branching points 231, 232 and 233. After the ramification the strands form interlaced loops. For example, the strand 212 ramifies at the branching point 232 into filaments 234, 235 and a strand 236. The filaments 234 and 235 form two corresponding loops. The strand 236 consisting of two remaining entwined filaments ramifies at a branching point 237 and provides a loop formed of the filaments 238 and 239. The loops formed thereby are interlaced so as to form a net structure.

Figure 2C:
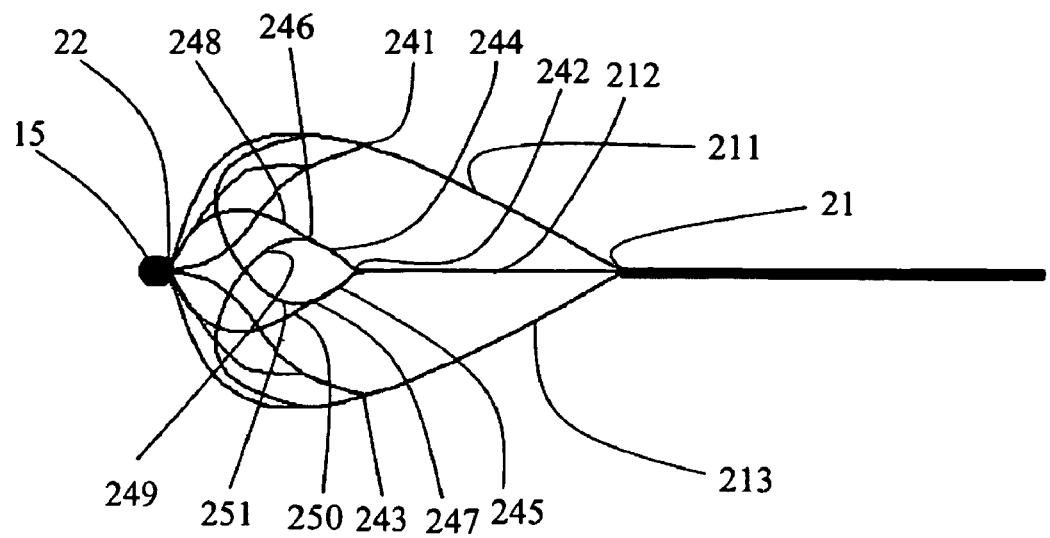

Referring now to FIG. 2C, yet another example of the retrieval basket 20 is illustrated. According to this example, the retrieval basket 20 includes four strands configured in branches. Only three such strands 211, 212 and 213 can be seen in FIG. 2C. Each strand is formed of four entwined wire filaments. The 211, 212 and 213 ramify at branching points 241, 242, 243 and result in interlaced loops. For example, the strand 212 ramifies at the branching point 242 into two branches 244 and 245, consisting of two entwined filaments. In turn, the branches 244 and 245 ramify at branching points 246 and 247, and provide loops formed of filaments 248, 249, 250 and 251, respectively. The loops formed thereby are interlaced so as to form a net structure.

Figure 2D:
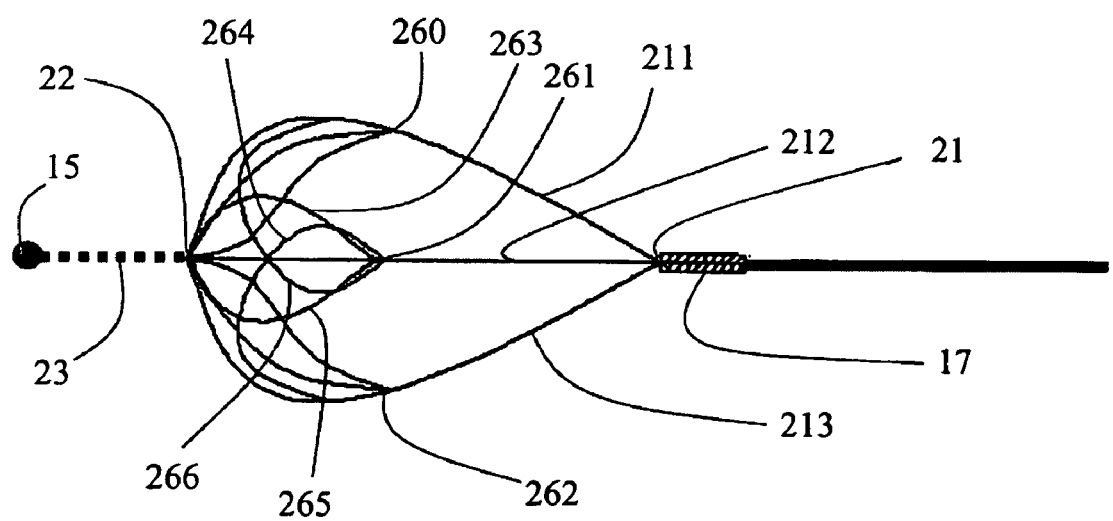

Referring now to FIG. 2D, still a further example of the retrieval basket 20 is illustrated. According to this example, the retrieval basket 20 includes four strands configured in branches. Only three such strands 212, 213 and 214 can be seen in FIG. 2D. Each strand is formed of four entwined wire filaments. These strands ramify at branching points 260, 261, 262 and result in interlaced loops. For example, the strand 212 ramifies at the branching point 261 into the loops formed of filaments 263, 264, 265 and 266. The loops formed thereby are interlaced so as to form a net structure. According to this embodiment of the invention, the strands of the basket are bound together at the proximal end 21 by means of the connector 17.

It is apparent that the retrieval basket of the present invention is not bound to the examples of the tipless baskets shown in FIG. 2A and FIG. 2B. If necessary, the basket may be constructed to have a tip at the distal end of the basket 22, for example, in by means of a bushing (15 in FIG. 2C and FIG. 2D), with the help of which the wire filaments are bound together. When desired, the tip 15 can be arranged at the distal end of a guiding rod (shown by dashed line 23 in FIG. 2D). The guiding rod 23 can, for example, be formed from intertwined wire filaments. The guiding rod 23 can function as a guide to facilitate the penetration and movement of the basket within the body organs.

Figure 2E:
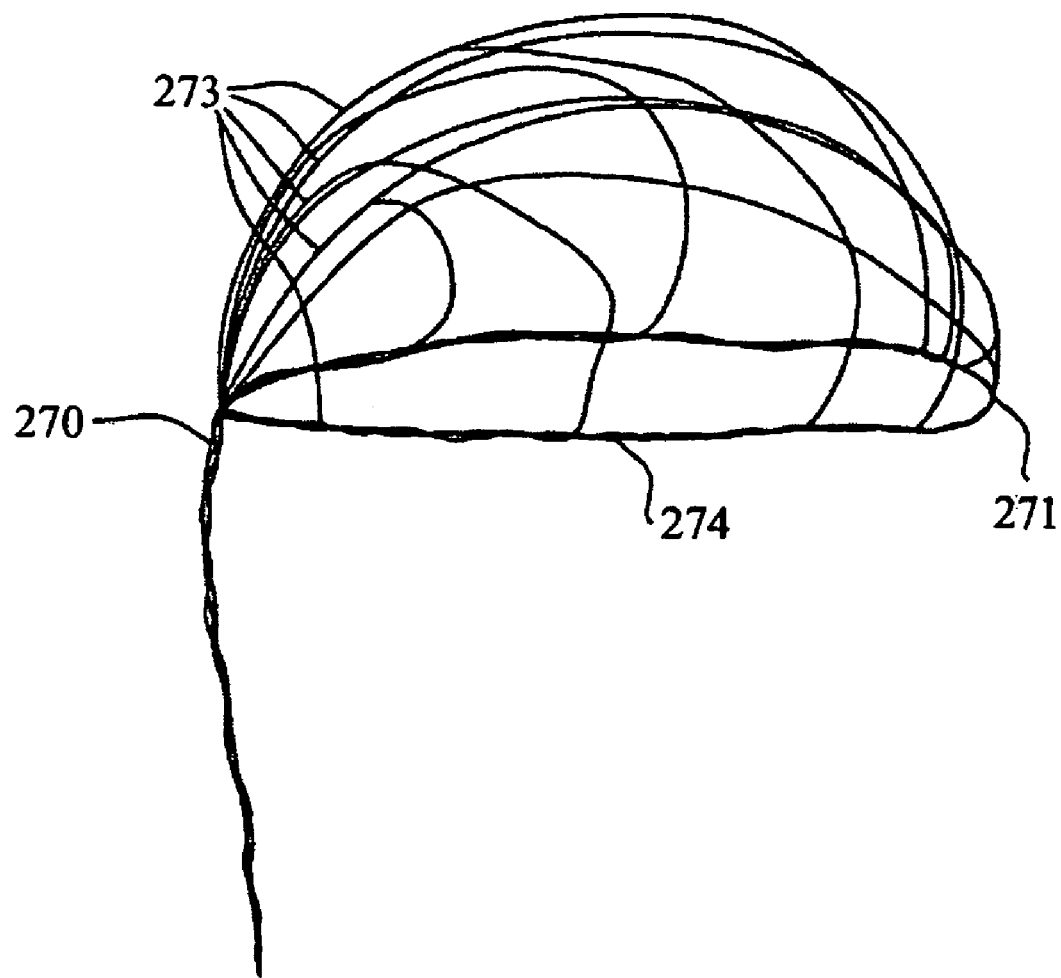

Referring now to FIG. 2E, still a further example of the retrieval basket 20 of the invention is illustrated. According to this example, the retrieval basket 20 comprises a spoon-like structure formed of a plurality of wire filaments. The basket 20 has a proximal end 271 and a distal end 272. In a region of the structure at the proximal end, the filaments are bound and form a plurality of strands 273. The filaments extend from the proximal end towards the distal end and are configured in the form of interlaced loops so as to form a net structure. The filaments, which originate from the proximal end, arrive at the proximal end after winding. According to this embodiment, one strand (a strand 274) of the plurality of strands 273 is common for all the filaments.

Referring now to FIGS. 10A-10F, it will be explained how individual wire filaments, from which the loops are made, could overlap and/or interlace. Note that the term "overlap" herein is assigned to such arrangement of the filaments, in which one element crosses another filaments, i.e., one of the filaments always being over or under the other filaments. The term "interlace" herein is assigned to the situation when at least one filament interweaves with the other filaments, i.e., one of the filaments passes first above the crossed filament and then passes under the next crossed filament.

In FIGS. 10A-10F different patterns corresponding to a possible arrangement of individual filaments defining the cells are shown schematically and with exaggeration. For the sake of simplicity, the wire filaments are depicted as vertical and horizontal bands overlapping at a right angle and defining orthogonal pattern, consisting of four vertical and four horizontal bands. However, it should be understood that in reality, thin wire filaments form the cells. The filaments are directed with respect to each other not necessarily at a right angle, and their amount is not limited to a four by four pattern.

Figure 10A:
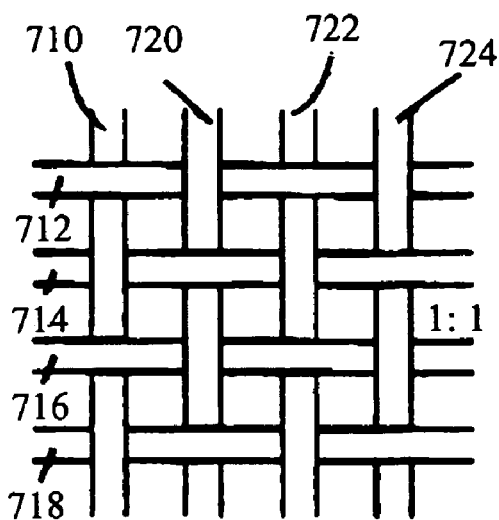
FIGS. 10A-10F illustrate schematically examples of how distal ends of the loops are intertwined.

FIG. 10A shows a pattern in which all wire filaments interlace one with another, i.e., each horizontal wire filament interlaces with all vertical filaments and vice versa. It is seen, for example, that a vertical filament 1010 goes first under a horizontal filament 1012, then above a horizontal filament 1014, then again under a horizontal filament 1016 and finally again above a horizontal filament 1018. On the other hand the horizontal filament 1012 goes first above the vertical filament 1010, then under a vertical filament 1020, then again above a vertical filament 1022 and then again under a vertical filament 1024. The rest of filaments are arranged similarly.

Figure 10B:
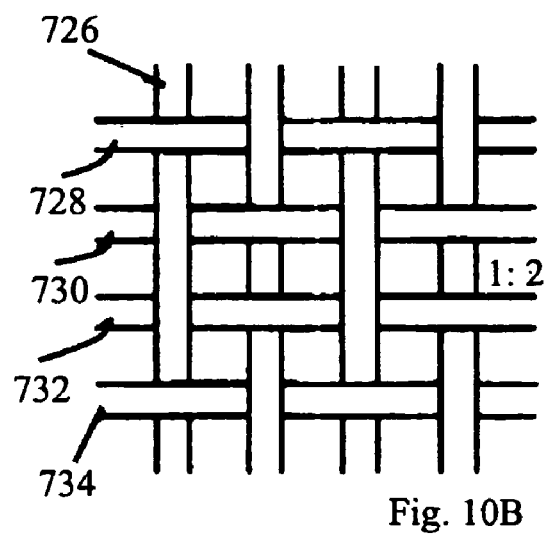

FIG. 10B depicts another situation, in which the filaments both interlace and overlap with intersection. It is seen that a vertical filament 1026 interlaces with horizontal filaments 1028, 1030, 1034 and overlaps with the perpendicularly directed filament 1032.

Figure 10C:
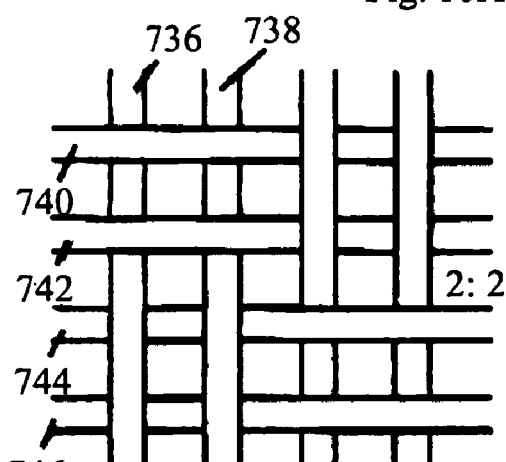

In FIG. 10C is shown still a new pattern, consisting of overlapped and interlaced filaments. It is seen for this example that two neighboring vertical filaments 1036, 1038 go under two neighboring horizontal filaments 1040, 1042 and then go above two next horizontal filaments 1044, 1046.

Figure 10D:
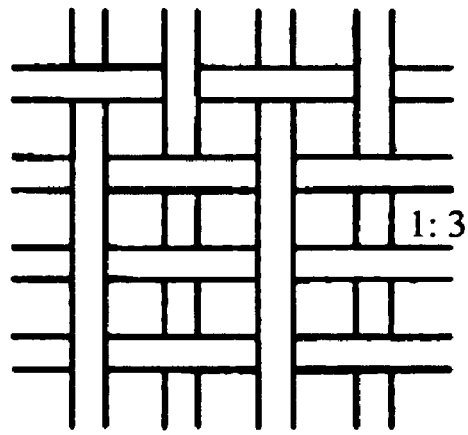
Figure 10F:
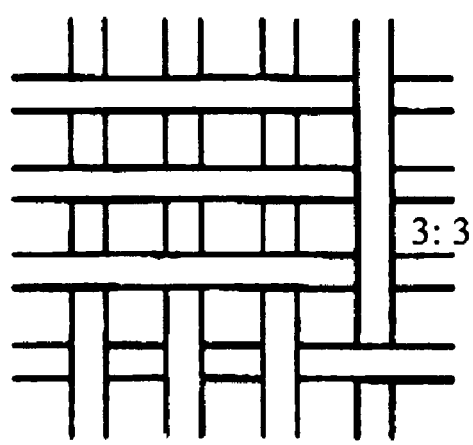
Figure 10E:
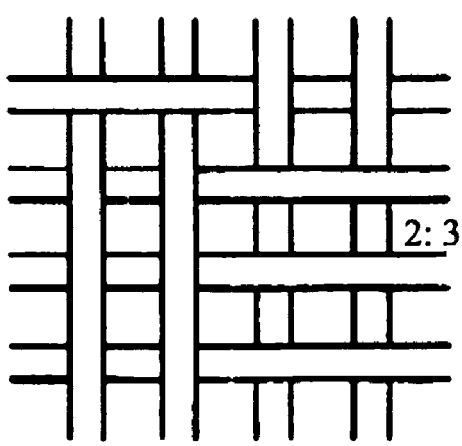

FIGS. 10D-10F show further possible patterns, consisting of overlapped and interlaced filaments. In particular, in the pattern shown in FIG. 10F, each filament overlaps with three perpendicular filaments and interlaces with only one filament.

It can be appreciated that the patterns depicted in FIG. 10A and FIG. 10F represent two extreme situations, corresponding respectively to the pattern in which all filaments are interlaced and to the pattern in which only one filament is interlaced, while the other filaments are overlapped.

Having explained various cells patterns, in which the filaments of the loops might be arranged, hereinbelow, a process of manufacturing the retrieval basket 20 (illustrated in FIG. 2A through FIG. 2F) will be described.

The process begins with a step of selection of a predetermined number of wires having a predetermined diameter and length.

According to one non-limiting example of the process, the manufacturing of the retrieval basket is carried out from one piece of wire.

According to another non-limiting example of the process the manufacturing of the retrieval basket is carried out from several wires.

It should be noted that the wires selected for the construction of the basket can be single-filament wires, or when desired, can be multi-filament wires.

Furthermore, the process for the fabrication of the retrieval basket includes weaving the retrieval basket from one piece of wire or from several wires.

For manufacturing a retrieval basket, according to the invention, at least a part of the weaving can be performed on a weaving jig. For this purpose, the jig can have a predetermined pattern formed by grooves configured on the jig's surface.

The manufacturing process also includes forming a shape of the retrieval basket that includes defining the basket's shape and topology (pattern). According to one embodiment of the invention, for the defining of the shape and topology at least a part of the filaments are bound on a shape-forming jig, which for this purpose has a predetermined shape.

The forming of the shape can further include shape storing annealing the basket mounted on the shape-forming jig. Such forming a shape allows the basket to impart the structural rigidity and dilatation abilities, when the basket is opened.

It should be appreciated that the weaving jig and the shape-forming jig can be the same unit or two different units, each having its own functions.

Figure 3:
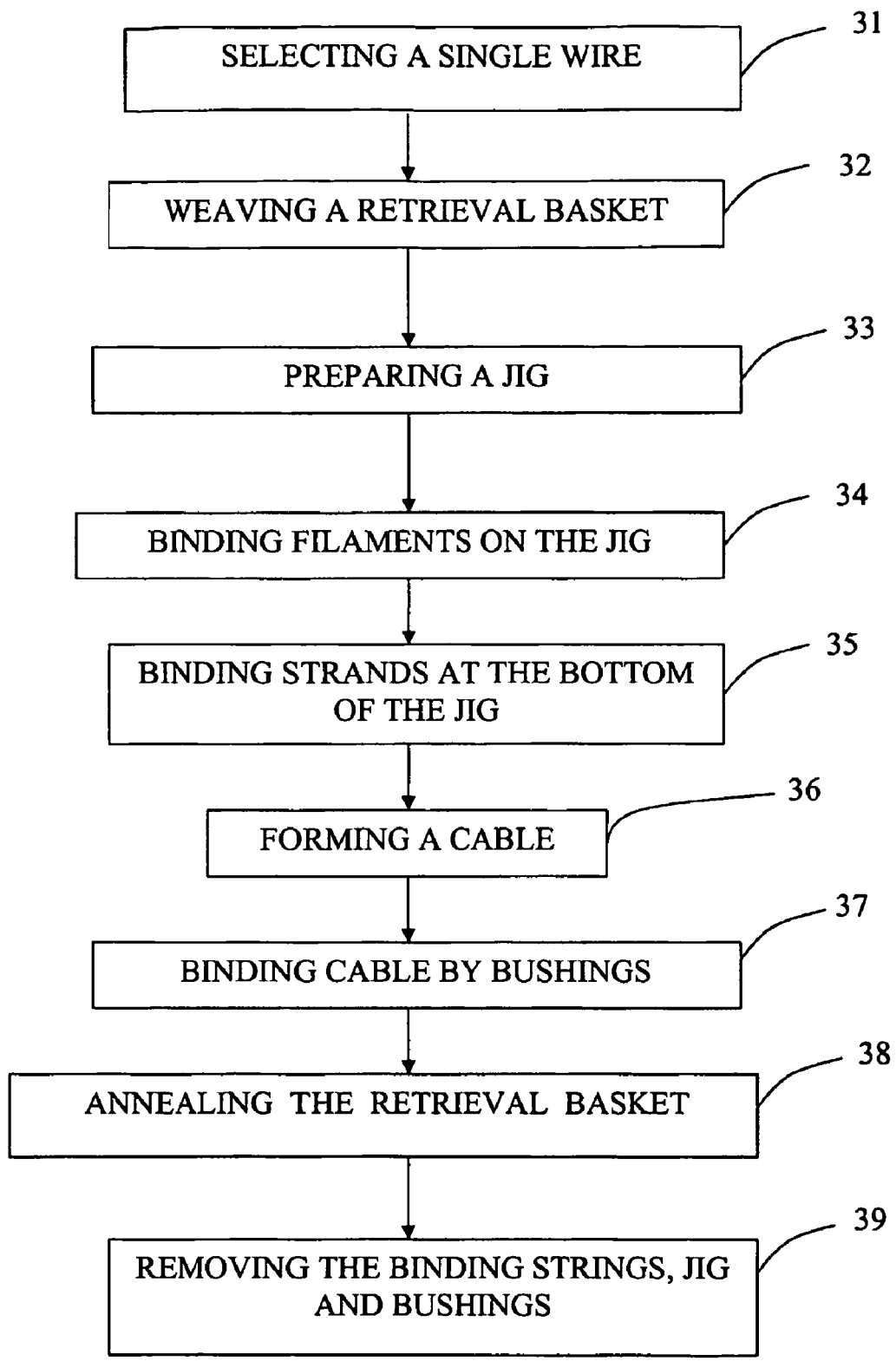
FIG. 3 is a flowchart diagram that describes the method for manufacturing a retrieval basket from a single wire piece, in accordance with one embodiment of this invention.

Referring now to FIG. 3, an example of the process for the fabrication of the retrieval basket 20 from a single piece of wire is described in detail. The process begins with a step 31 of selection of a single wire having a predetermined diameter and length. It should be appreciated that this length depends on the shape, pattern and size of the basket 20. For example, for a basket having the size of 3 Fr, the minimal diameter and length of the wire selected for the retrieval basket 20 is about 0.1 mm Fr and 100 cm, respectively.

Typically, the wire utilized for the fabrication of the retrieval basket 20 is made of a suitable shape memory or elastic material. According to one embodiment of the invention, the wire is made of metallic material. The metallic material can be selected from NiTi based alloy (e.g., Nitinol) and stainless steel.

According to another embodiment of the invention, the wire is made of non-metallic material, e.g. Capron.

According to a still further embodiment of the invention, the filaments of the basket are covered by an insulating layer. The insulating layer can, for example, be made of Teflon. The advantage of Teflon is its thermal resistance and low coefficient of mechanical friction, which leads to an additional reduction of traumatism.

According to yet another embodiment of the invention, the wire is made of a material that has thermo-mechanical shape memory characteristics.

As was noted above, the wire selected for the construction of the basket can be a single-filament wire, or, when desired, can be a multi-filament wire.

Referring to FIG. 3 and FIGS. 5A-5C together, the process for the fabrication of the retrieval basket 20 further includes a step 32 of weaving the retrieval basket from the selected single wire, according to one embodiment of the invention. According to this embodiment, the process includes a step 33 of preparing a jig 52 designed for weaving and shaping the basket 20. The jig 52 can have a structure including grooves arranged in accordance with the desired pattern of the basket 20 and can have a shape that imitates the desired shape of the basket 20.

According to this embodiment, one end 51 of the single wire piece is fixed, while the other end is put on the top part of the jig 52 and moved along the grooves in accordance with a desired pattern of the weaving and topology of the basket structure. The weaving of the basket continues by moving the free end away from the jig and returning it thereto by overlapping and/or interlacing the wire filaments, as long as required to form a net.

Figure 5A:
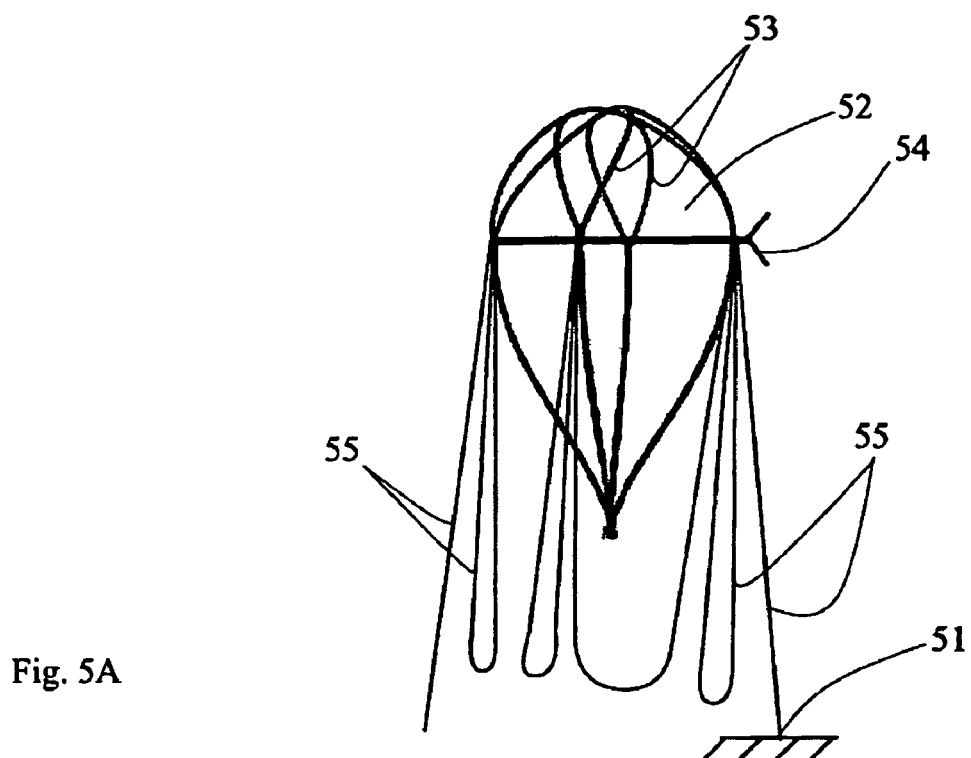
FIGS. 5A-5C are illustrations of the steps of the method for manufacturing a retrieval basket, in accordance with one embodiment of the invention.

In order to avoid the slipping down of the wire from the jig and unweaving of the basket, filaments 53 woven thereby are tied up (step 34) on the jig 52 by a first string 54 worn round the jig, as shown in FIG. 5A. An example of the first string includes, but is not limited to, a copper wire having strength sufficient to maintain the fixture of the basket on the jig.

Figure 5B:
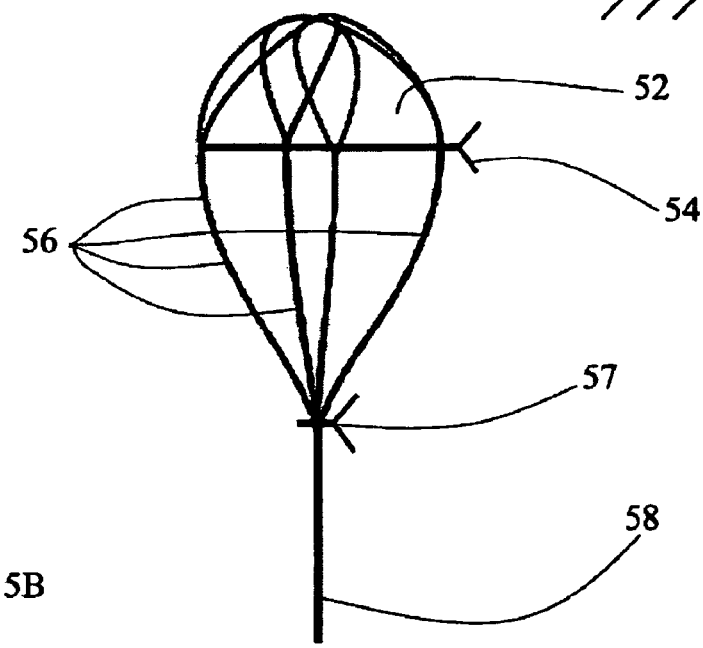

Further, the fixed end (51 in FIG. 5A) of the wire is released, and filaments 55 dangled from the jig are bound together to form strands 56, as shown in FIG. 5B. The strands 56 are in turn tied up by a second string 57 at the bottom part of the jig 52 for defining a shape of the basket (step 35). An example of the second string includes, but is not limited to, a copper wire having sufficient strength to maintain the strands 56 together. The strands 56 are then bound together (step 36) to form a cable 58.

Thereafter, two temporary bushings 59a and 59b are put on the ends of the cable 58 (step 37). The bushings 59a and 59b can, for example, be in the form of pipes made of metal, e.g., Ni, stainless steel, etc. The bushings 59a and 59b are then squeezed (crimped) for reducing their inner diameter, and thus fixation of the filaments therein. It should be appreciated that this is only a non-limiting example of the filaments' fixation. Other ways can also be used, e.g., soldering, welding or gluing. When desired, the ends of the bushings 59a and 59b (for fixation on the cable 58) can be further additionally treated by soldering, welding and/or polishing.

Specifically, for a metallic basket having the size of 3 Fr, according to the example described above, the bushings can have the inner diameter of 0.7 mm and the length of 4 mm. After squeezing, the inner diameter of the bushings 59a and 59b put on the cable 58, can, for example, achieve a value of 0.6 mm. It should be understood that these values can be varied depending on the wire's material, construction, etc.

The process of FIG. 3 further includes a step 38 of shape storing annealing that depends on the materials of the wire. For example, when such material is Nitinol, the annealing is carried out at the temperature of about 450° C.-600° C. over at least about 10 min. It should be appreciated that such heat treatments could relieve internal stresses in the material and provide the memorization of the basket shape.

It should be appreciated that the invention is not limited to the specific implementation of the annealing step. For example, the annealing can be carried out in an oven configured for this purpose. However, when the wire is selected from a conductive material, the annealing can be carried out by passing electric current through the filaments of the basket.

After the annealing, the jig 52, the first string 54, the second string 57 and the temporary bushings 59a and 59b are removed (step 39).

It should be appreciated that the process of manufacturing the retrieval basket is not limited to forming the basket from one piece of wire. According to another example, the retrieval basket can also be formed from several wires.

Figure 4:
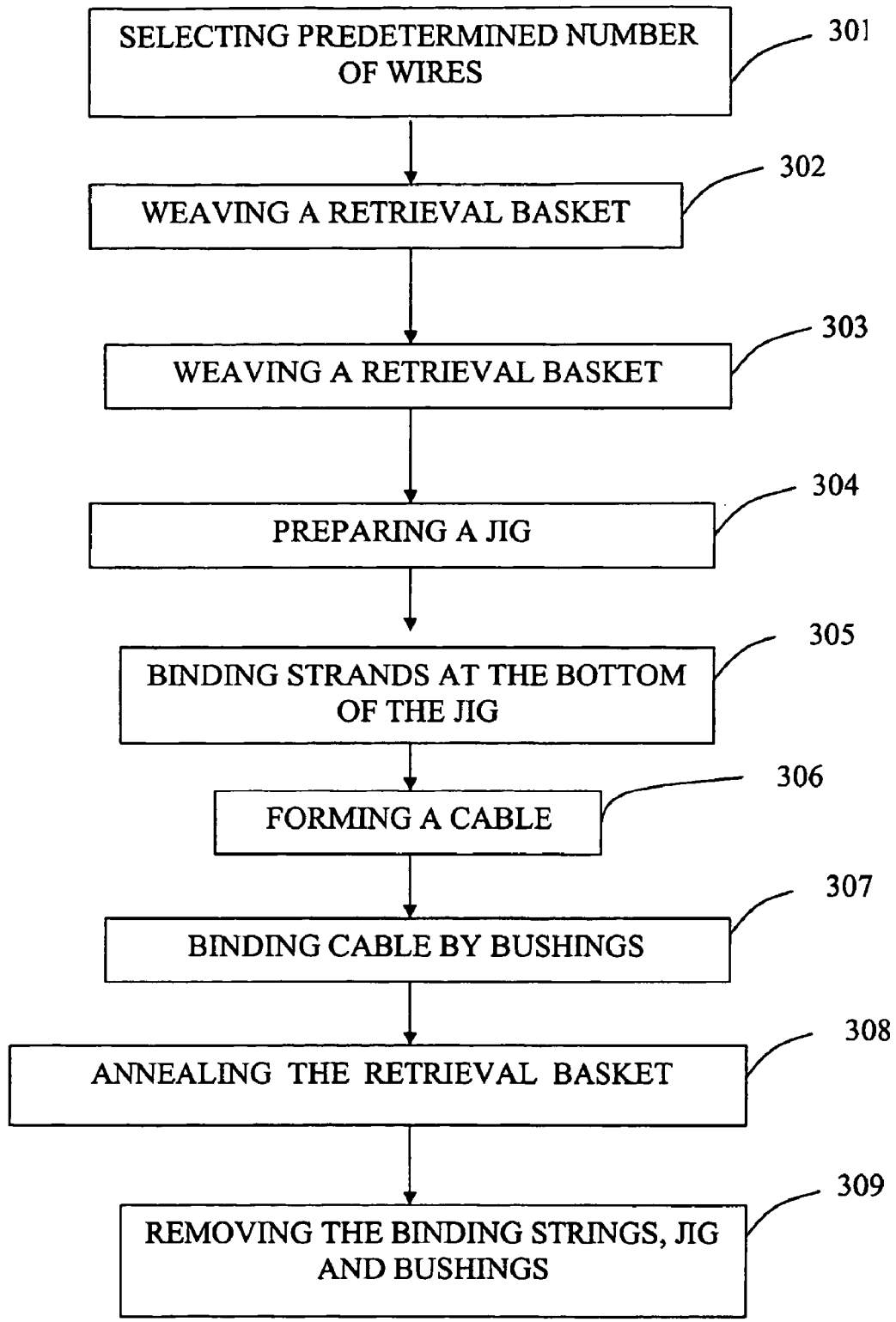
FIG. 4 is a flowchart diagram that describes the method for manufacturing a retrieval basket from several wires, in accordance with another embodiment of this invention.

Referring now to FIG. 4, a further example of the process for fabrication of the retrieval basket 20 from several wires is shown in detail. The process begins with a step 301 of selection of a predetermined number of wires having a predetermined diameter and length. It should be appreciated that the choice of the wire parameters depends on the shape, pattern and size of the basket. For example, for a basket shown in FIG. 2A and having the size of 3 Fr, the number of the wires is 8, the minimal diameter and length of the wires are 0.12 mm and 100 cm, respectively.

The process for fabrication of the retrieval basket includes a step 302 of weaving the retrieval basket from the selected number of wires.

According to one example, the process includes a step 303 of preparing a jig 41 designed for weaving the basket 20. In particular, the jig 52 suitable for the process of fabrication of the basket from a single piece of wire is also suitable for the process shown in FIG. 4.

For purpose of this embodiment of the process shown in FIG. 4, firstly, a wire is selected. One end of this wire is moved along the grooves of the jig in accordance with a desired pattern of the weaving. When this wire is dropped into the grooves, the free ends of the wires are placed at the bottom of the jig. Thereafter, another wire is taken, and the process continues with this wire. As a result of such weaving, the wire filaments are intercrossed and/or interlaced in accordance with the desired topology of the basket structure.

The further steps of the process shown in FIG. 4 for forming the basket from several wires are similar to the process steps 34 through 39 of FIG. 3A. Accordingly, the process further includes the steps of binding the wire filaments on the jig (step 304) by a first string; forming strands and the binding thereof at the bottom of the jig (step 305) by a second string; bounding the strands and forming a cable (step 306); binding the cable by bushings (step 307); annealing the basket (step 308); and removing the jig along with the binding strings and bushings (step 309).

Figure 6:
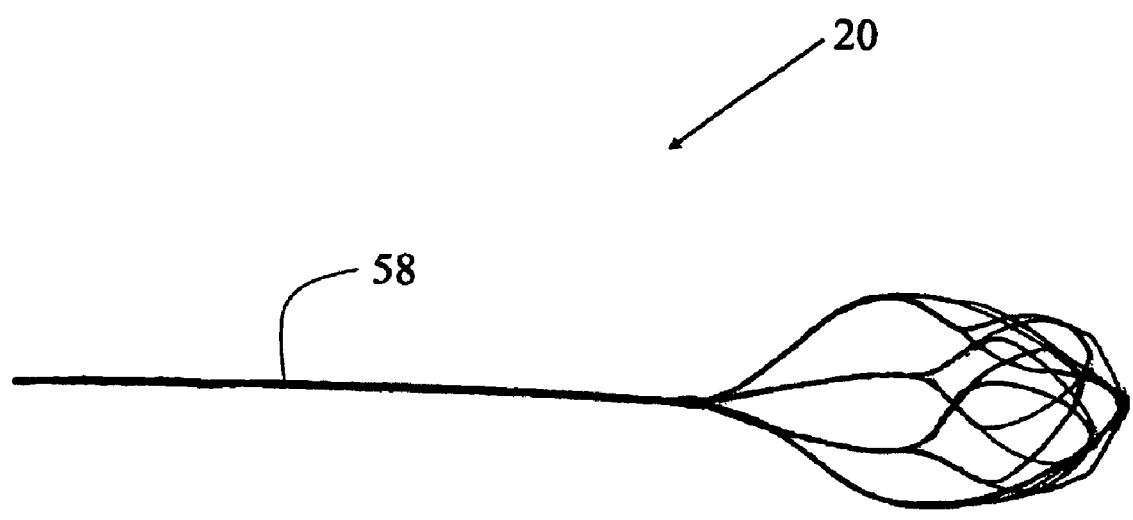
FIG. 6 is an example of the basket obtained by the process of FIG. 3.

Accordingly, FIG. 6 shows an example of the basket obtained by the process shown in FIG. 3 or FIG. 4.

It should be appreciated that when required, the process for the fabrication of the retrieval basket can include a step of binding the filaments at the distal end 22 together to form a basket tip. Such binding can, for example, be done by a bushing. When desired, after the tip, the wire filaments can be extended to form a guiding rod (shown by dashed line 23 in FIG. 2D).

Figure 11A:
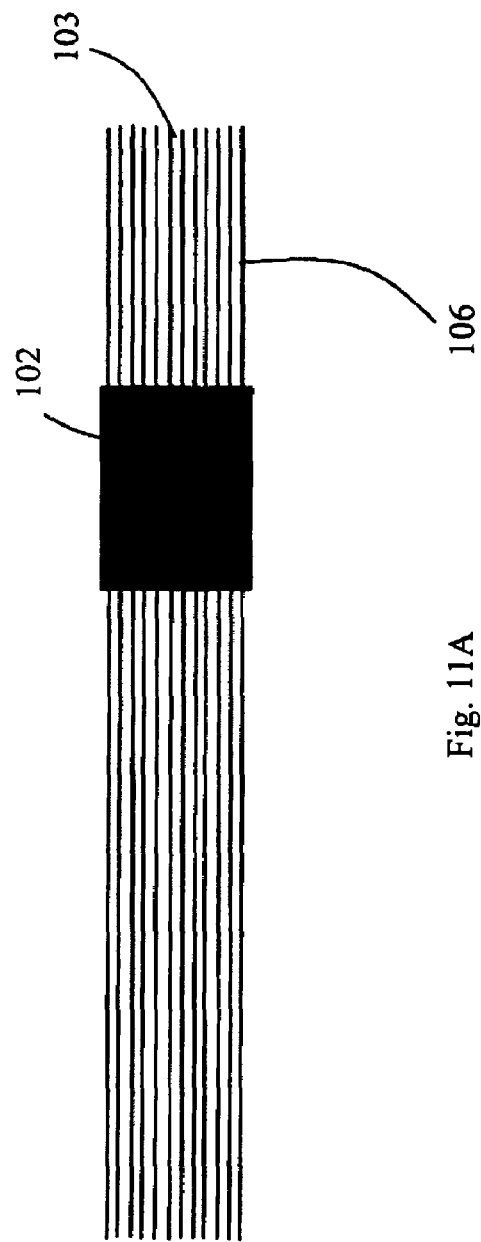
FIGS. 11A-11B are illustrations of the method for manufacturing a retrieval basket, in accordance with a further embodiment of the invention.
Figure 11B:
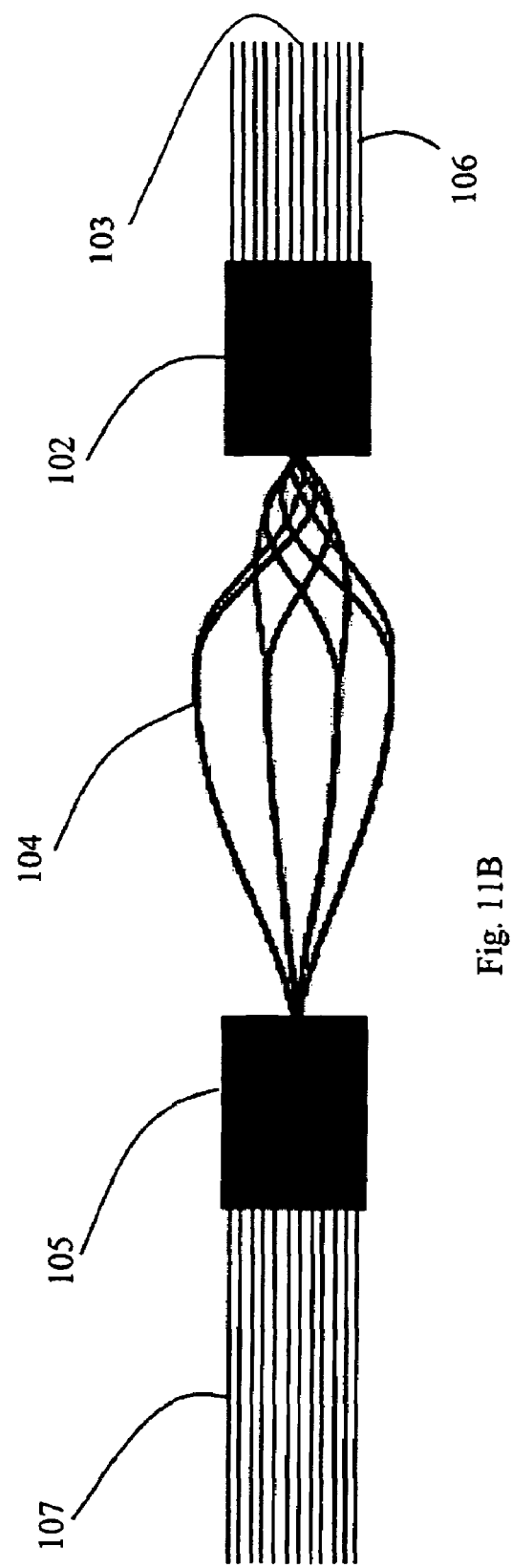

Referring to FIGS. 11A and 11B together, a still further example of the process for fabrication of the retrieval basket 20 from several wires is shown in detail.

The process starts with a step of selection of a predetermined number of wires having a predetermined diameter and length. It should be appreciated that the choice of the parameters of the wires depends on the shape, pattern and size of the basket.

Furthermore, the process for fabrication of the retrieval basket includes a step of weaving the retrieval basket from the selected number of wires. For this purpose, the wires are joined together in a bunch 101, and then, a bushing 102 is fixed on the bunch 101 at a predetermined distance from an end 103 of the bunch 101. A section 106 of the bunch 101 between the bushing 102 and the end 103 is devised for forming a guide rod. Therefore, the length of this distance depends on the desired length of the guide rod. The basket is woven by overlapping and/or interlacing the wire filaments so that to form a net 104. After the weaving, another bushing 105 is fixed on the bunch 101, in order to avoid the unweaving of the basket.

Thereafter, the process for fabrication of the retrieval basket includes a step of forming a basket's shape. For this purpose, the basket is mounted, aligned and fixed on a shape-forming jig (not shown), which has a predetermined shape. Further, the step of forming a basket's shape includes shape storing annealing. For example, when the wires are selected from Nitinol, the annealing can be carried out at the temperature of about 400° C.-600° C. over at least about 10 min.

According to one embodiment of the invention, the heating at such temperatures can be performed in an oven. According to another embodiment of the invention, the heating at such temperatures can be performed by passing an electric current through the wire filaments.

Furthermore, when required, the process for fabrication of the retrieval basket can include a step of forming a guide rod. For this purpose, a certain number of superfluous wire filaments in the section 106 are cut off, and the remaining wire filaments are twisted together. Preferably, the twisted wire filaments are then squeezed and heated. The heating can, for example, be performed by applying a voltage (e.g., about 4 V over about 2-3 sec) across the section 106.

Figure 5C:
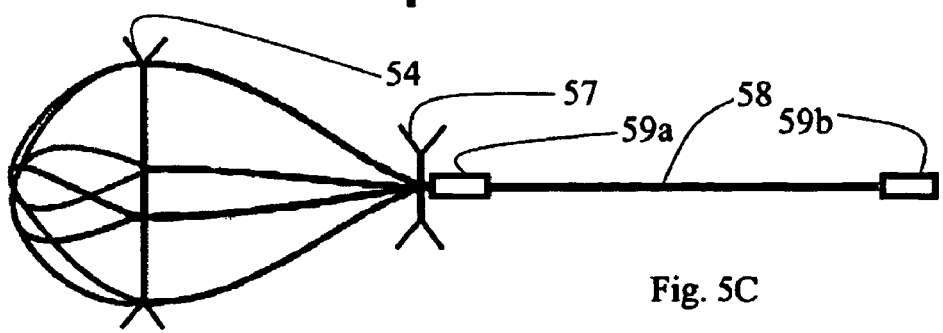

The process for fabrication of the retrieval basket can include a step of bounding the wire filaments of a section 107 and forming a cable (that is similar to the cable 58 in FIGS. 5B-5C). The forming of the cable can, for example, be performed by twisting and squeezing the filaments and applying a voltage (e.g., about 20-30 V over about 3-10 sec) across the section 107.

Those skilled in the art will now recognize the substantial difference between the prior art retrieval basket of FIG. 1 and the retrieval basket of FIGS. 2A-2E produced by the novel process of the present invention. In particular, according to the prior art methods, the baskets are assembled from a number of wires having the predetermined configuration along a basket axis with the wire ends binding together at the proximal and distal ends. In contrast to the prior art techniques, the novel process of the present invention is based on weaving the basket such that the wire loops formed as a result of the weaving of the filaments are interlaced so as to define a net, and thereby to impart an enhanced structural rigidity and dilatation ability to the basket.

From the foregoing description it should be appreciated that retrieval baskets constructed in accordance with the present invention can comprise a variety of user desired shapes, number of wires, topology of weaving, and filament spacing.

The basket manufactured from a single wire or several wires as described above, can be used in the production of a surgical device for extracting objects from a body during the treatment of the biliary or urinary systems. Such treatment may include the extraction of stones, e.g., gall stones, kidney stones, etc.

Figure 7:
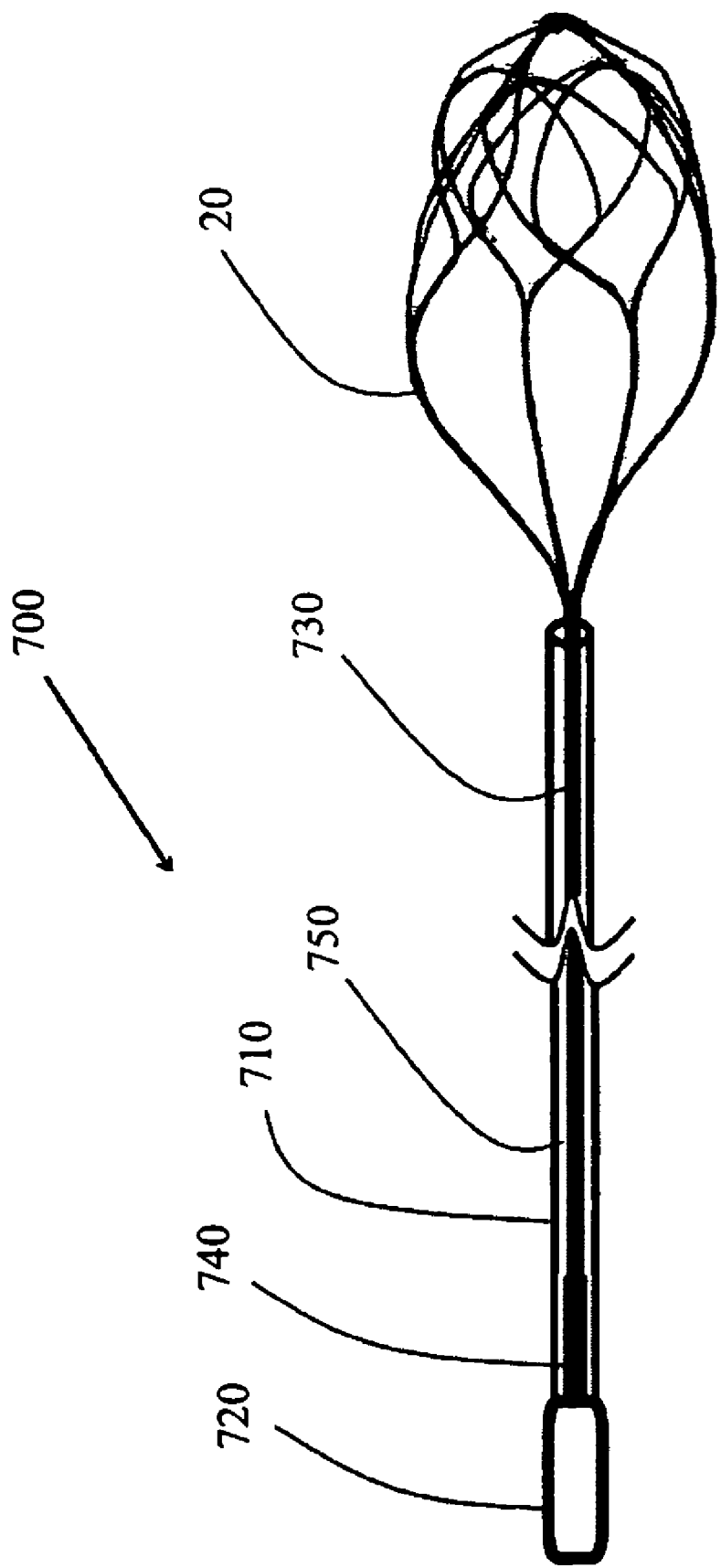
FIG. 7 is a schematic view of a surgical device for extraction of an object from a body, according to one embodiment of the invention.

Referring now to FIG. 7, a schematic view of a surgical device 700 for extraction of an object from a body is shown, according to one embodiment of the invention. The device 700 includes the retrieval basket 20 obtained by the method described above, a flexible tubular catheter 710, configured as a sheath, adapted to penetrate along the body passages near the location of the object (not shown), and a manipulator 720 suitable for manipulating the retrieval basket 20.

It can be appreciated by a person versed in the art that in contrast to the conventional extractor (shown in FIG. 1), the device of the present invention depicted in FIG. 2A through FIG. 2C does not include the connector (17 in FIG. 1). Additionally, a manipulation cable 730 located within the catheter 710 includes the cable 58 that is formed as an integral part of the basket 20. In other words, the manipulation cable 730 is not a separate element (cable 12 in FIG. 1). It can be appreciated that when the cable 58 itself is used as the manipulation cable, then it is directly connected to the manipulator 720. Such connection can be performed, for example, by soldering. However, when the length of the cable 58 is not sufficient for manipulating the surgical device, the manipulation cable 730 can include the cable 58 and a pushing element 740 (e.g., rod, cable or wire), also arranged within the catheter. In this case, the pushing element 740 is connected to the manipulator 720 (at one end) and the cable 58 (at another end), thereby extending the manipulation cable length.

In practice, a surgeon can manipulate the cable or pushing element by means of the manipulator 720, and thus the basket 20 can be either retracted within the catheter 710 or protracted therefrom. The surgeon, by holding the manipulator 720, can also maneuver the catheter 710 within the body organ (not shown), (e.g. to displace it by turning, pushing or pulling).

Figure 8:
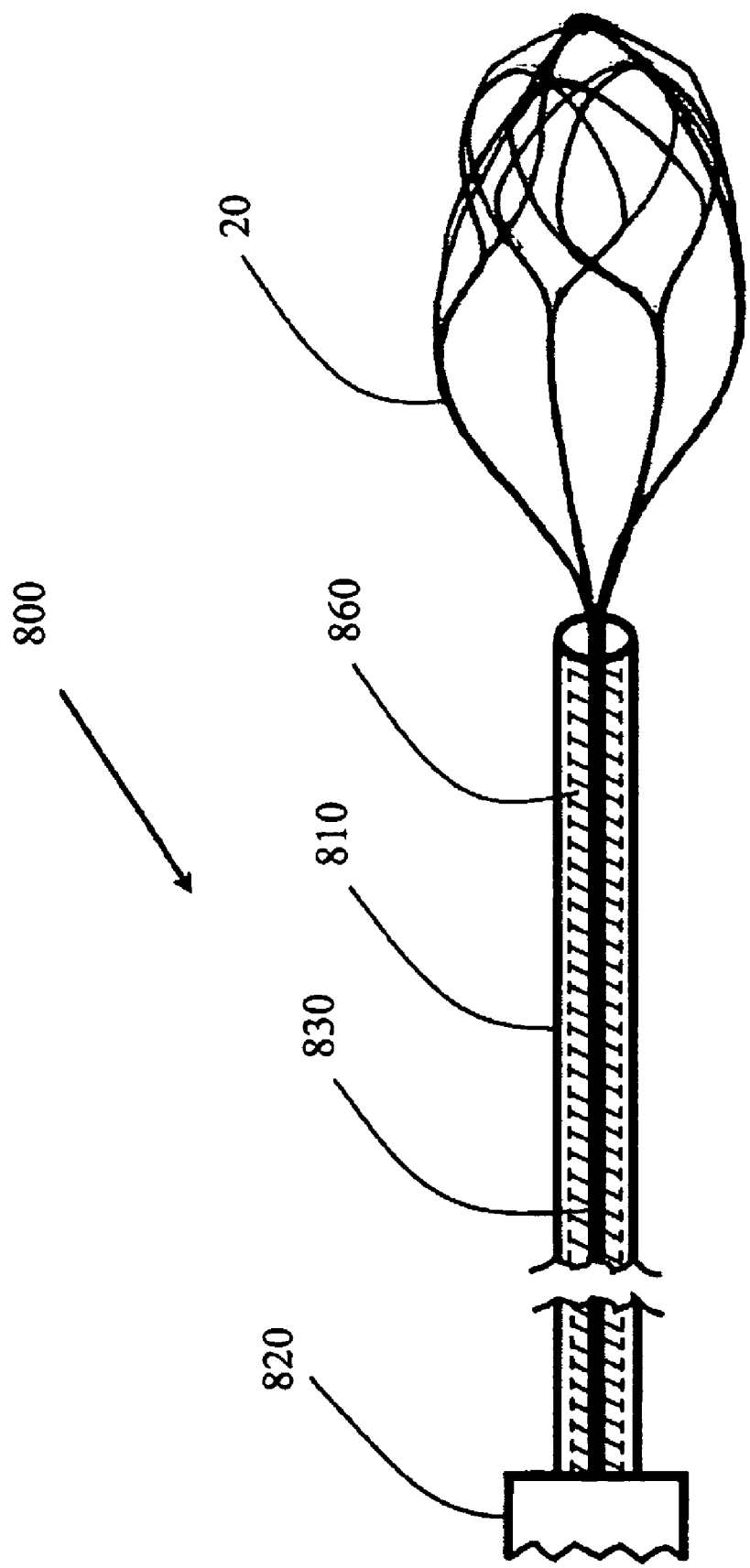
FIG. 8 is a schematic view of a surgical device for extraction of an object from a body, according to another embodiment of the invention.

Referring to FIG. 8, a schematic view of a surgical device 800 for extraction of an object from a body is shown, according to another embodiment of the invention.

This embodiment of the invention is devised for overcoming the aforementioned drawback of the conventional surgical extractor (10 in FIG. 1) and inherent also to the surgical device (700 in FIG. 7), which is associated with the discrepancy of the inner diameter of the catheter and the diameter of the manipulation cable. As can be appreciated by a person versed in the art, due to this discrepancy, an air gap (18 in FIGS. 1 and 750 in FIG. 7) between the inner wall of the catheter and the manipulation cable significantly affects the deformation properties of the catheter and the ability of the catheter to bend without destruction on large angles.

The device 800 includes the retrieval basket 20 obtained by the method described above, a flexible tubular catheter 810, configured as a sheath, a manipulator 820, manipulation cable 830 located within the catheter 810, and a filling tubing 860. According to this embodiment of the invention, the filling tubing 860 is put on a major portion of the manipulation cable 830 that is formed from the cable 58.

The outer diameter of the filling tubing 860 should have a sufficient magnitude to substantially fill the gap between the inner wall of the catheter 810 and the manipulation cable 830, in order to enhance the ability of the catheter to bend without destruction on large angles, while enabling for the manipulation cable 830 to move without significant friction within the catheter.

According to one embodiment of the invention, the filling tubing 860 is formed of a heat-shrinking material. An examples of the heat-shrinking tubings includes, but are not limited to, PTFE heat-shrinking tubing SLW-HS NATURAL available from ZEUS.

A process for preparing the surgical device 800 includes putting the filling tubing 860 on the cable (58 in FIG. 6) of the basket 20 manufactured according to the method described above, and heating the assembly obtained thereby at the temperature of 80° C.-120° C. over at least about 1 min.

Figure 9:
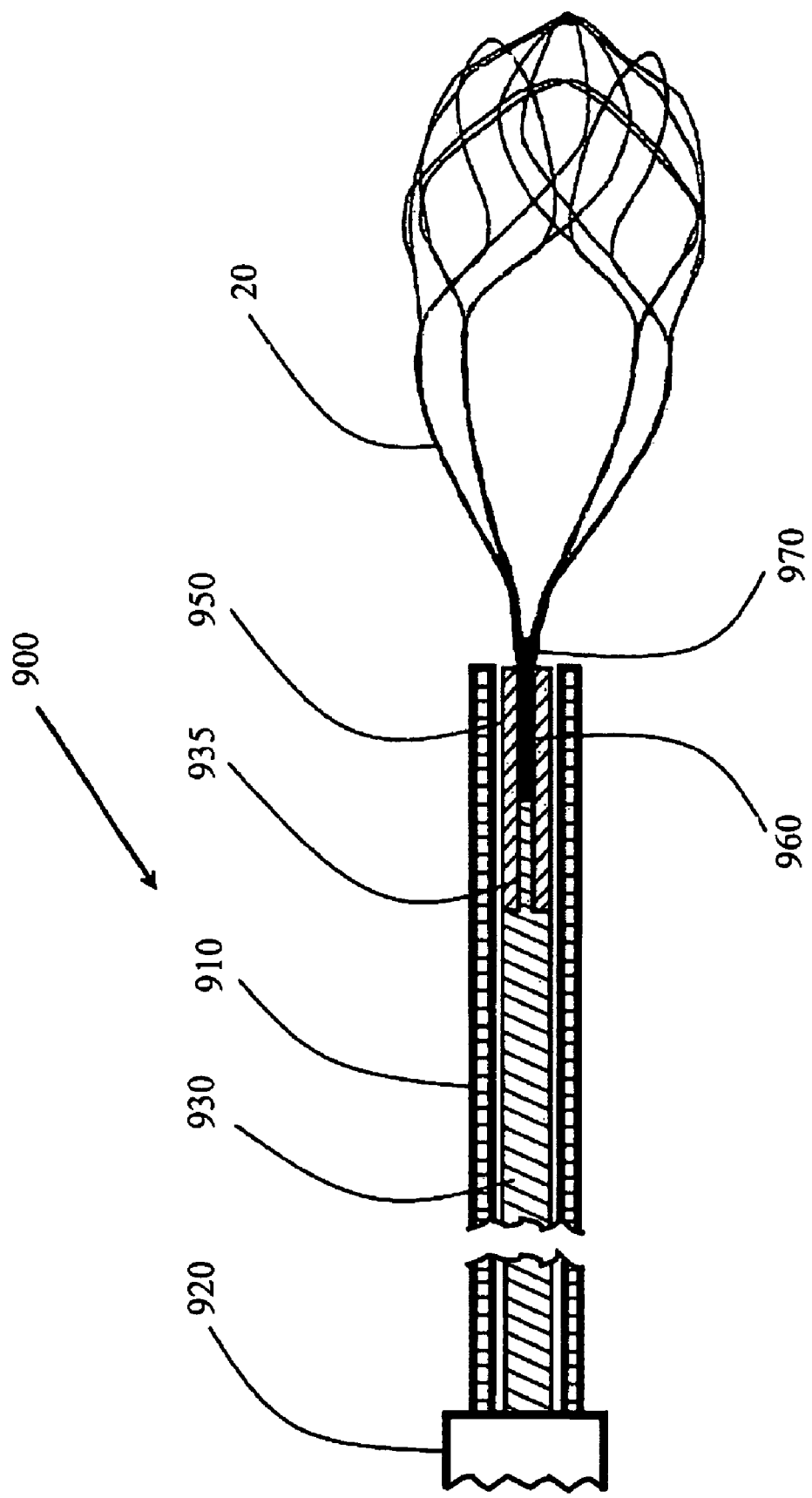
FIG. 9 is a schematic view of a surgical device for extraction of an object from a body, according to yet another embodiment of the invention.

Referring to FIG. 9, a schematic view of a surgical device 900 for extraction of an object from a body is shown, according to yet another embodiment of the invention. The device 900 includes the retrieval basket 20 obtained by the method described above, a flexible tubular catheter 910, configured as a sheath, a manipulator 920, and a manipulation cable 930 located within the catheter 910.

According to this embodiment of the invention, the manipulation cable 930 is produced as a separate unit. In this case it is coupled to the manipulator 920 at a cable proximal end 934 and to a common basket strand 960 at a cable distal end 935. The joint between the common strand 960 and the cable distal end 935 is accomplished by means of a bushing 950. The common strand 960 is a portion of the cable 58 that is cut in the vicinity of an original branching point 970 of the basket 20. The bushing 950 can, for example, be in the form of a pipe made of Ni, stainless steel, etc.

In order to enhance the ability of the catheter to bend without destruction on large angles the diameter of the major portion of the manipulation cable 930 has a magnitude sufficient to fill substantially the gap between the inner wall of the catheter 910 and the manipulation cable 930. The diameter of the manipulation cable 930 at the distal end 935 is different from its major diameter and has a magnitude substantially close to the magnitude of the common basket strand 960.

In order to obtain a joint between the manipulation cable 930 and the common basket strand 960 the process for preparing the surgical device 900 includes providing the bushing 950; putting the bushing 950 on a portion of the common basket strand 960 and on the distal end 935; and squeezing the bushing 950 for reduction of its inner diameter to the magnitude sufficient to maintain the joint. According to one embodiment, the magnitude of the diameter of the bushing after such squeezing is close to a magnitude of the major diameter of the manipulation cable.

As such, those skilled in the art to which the present invention pertains, can appreciate that while the present invention has been described in terms of preferred embodiments, the concept upon which this disclosure is based may readily be utilized as a basis for the designing of other structures and processes for carrying out the several purposes of the present invention.

It should be understood that the device of the present invention is not limited to the urological treatment of a human body. It can be successfully employed for surgical treatments of animals as well. Furthermore, the present invention is not limited strictly to fabrication of a surgical device for extracting calculi during the urological treatment. Such a device is suitable for other surgical treatments, which might require retrieval of foreign objects from the body systems, e.g. from blood vessels etc.

Moreover, the present invention is not limited to fabrication of medical devices, and the extractor device can be used to extract any type of article from a wide range of inaccessible locations such as inside a pipe or tube (for example, the waste outlet of a domestic sink) or inside a chamber within a large piece of machinery which would be difficult to dismantle.

In the method claims that follow, alphabetic characters used to designate claim steps are provided for convenience only and do not imply any particular order of performing the steps.

Also, it is to be understood that the phraseology and terminology employed herein are for the purpose of description and should not be regarded as limiting.

It is important, therefore, that the scope of the invention is not construed as being limited by the illustrative embodiments set forth herein. Other variations are possible within the scope of the present invention as defined in the appended claims and their equivalents.

The invention claimed is:

1. A method for manufacturing a retrieval basket having a proximal end and a distal end and constituted by a plurality of wire filaments extending from the proximal end towards the distal end, comprising:
   selecting at least one wire;
   weaving the basket from the wire, wherein said weaving includes forming portions from wire filaments that are bound together to define a plurality of strands, said plurality of strands ramify at corresponding branching points into loops having various shapes and sizes, at least a part of the loops are overlapped and/or interlaced at spaced points so as to define a net at least in the vicinity of, and spaced from the distal end; and
   forming a shape of the retrieval basket, thereby imparting structural rigidity and dilatation abilities to the basket when opened.

2. The method of claim 1 further including binding the strands together at said proximal end for forming a manipulation cable.

3. The method of claim 2 further including binding the filaments of the manipulation cable by temporary bushings.

4. The method of claim 3 further including annealing said retrieval basket.

5. The method of claim 1 including binding the filaments at the distal end together for forming a basket tip.

6. The method of claim 4 wherein the wire is made of metallic material.

7. The method of claim 6 wherein said metallic material has thermo- mechanical shape memory characteristic.

8. The method of claim 6 wherein said metallic material has supereleastic characteristic.

9. The method of claim 6 wherein said metallic material is selected from NiTi based alloy and stainless steel.

10. The method of claim 9 wherein said annealing is carried out at the temperature in the range of about 450° C. - 600° C.

11. The method of claim 1 wherein said forming of the shape includes preparing a shape-forming jig having a predetermined shape.

12. The method of claim 11 wherein said forming of the shape includes binding the filaments and the strands on said shape-forming jig.

13. The method of claim 12 wherein said forming of the shape further includes annealing said retrieval basket.

14. The method of claim 1 wherein said weaving includes preparing a weaving jig having a predetermined a pattern formed by grooves configured on a surface of the jig.

15. The method of claim 14 wherein at least a part of the weaving of the basket is performed on said weaving jig, wherein said weaving includes
   fixing one end of the wire, while the other end is putting on the top part of the jig; and
   moving the free end along the grooves by taking it away from the jig and returning it thereto together with overlapping and/or interlacing the wire filaments, in accordance with a desired pattern of the weaving and topology of the basket structure.

16. The method of claim 1 wherein said weaving of the basket includes:
   selecting a predetermined number of wires;
   joining the wires together in a bunch;
   fixing a bushing on the bunch at a predetermined distance from an end of the bunch;
   overlapping and/or interlacing the wire filaments so that to form a net;
   fixing another bushing on the bunch, thereby to avoid unweaving of the net.

17. The method of claim 16 further including a step of forming a guide rod that includes cutting of a certain number of the wire filaments at the distal end; and twisting the remaining number of the filaments together.

18. The method of claim 1 wherein the filaments in a region of the structure at the proximal end form a plurality of strands, where one of the strands is common for all the filaments.

19. The method of claim 1 wherein said shape is a parachute-like shape.

20. The method of claim 1 wherein said shape is a spoon-like shape.

21. The method of claim 1 wherein the wire are made of non-metallic material.

22. The method of claim 21 wherein said non-metallic material is Capron.

23. The method of claim 1 wherein the filaments are covered by a coating layer.

24. The method of claim 23 wherein said coating layer is made of Teflon.

25. A method of manufacturing a surgical device for removing a foreign object from a body, comprising:
   providing a retrieval basket fabricated according to claim 1 configured for entrapping and retaining the object located in the body for its extraction therefrom;
   providing a basket control assembly comprising a tubular sheath adapted to penetrate into the body for reaching the object, a manipulator for manipulating the basket for extraction the object from the body, and a manipulation cable arranged within the sheath for connecting the basket to the manipulator, where the assembly is configured for retracting the basket within the sheath and protracting the basket therefrom for its opening; and
   coupling the retrieval basket to the basket control assembly.

26. The method of claim 25 wherein said manipulation cable is constituted by said plurality of filaments extending from said proximal end towards the manipulator.

27. The method of claim 25 further comprising the step of providing a filling tubing and putting thereof at least on a portion of said manipulation cable.

28. The method of claim 27 wherein a magnitude of diameter of said filling tubing is sufficient to fill a gap between an inner wall of the catheter and the manipulation cable.

29. The method of claim 25 wherein said manipulation cable is configured as a separaLe unit selected from a rod, cable and wire.

30. The method of claim 29 wherein a joint between a common basket strand of the basket and the manipulation cable is established by means of a bushing.

31. The method of claim 30 wherein at least a portion of said manipulation cable has a magnitude of diameter sufficient to substantially eliminate any gap between an inner wall of the catheter and the manipulation cable.

32. The method of claim 30 wherein a magnitude of diameter of the bushing and a magnitude of diameter of at least a portion of said manipulation cable are close to one another.

* * * * *

UNITED STATES PATENT AND TRADEMARK OFFICE
CERTIFICATE OF CORRECTION

PATENT NO. : 7,640,952 B2  Page 1 of 1
APPLICATION NO. : 11/159396
DATED : January 5, 2010
INVENTOR(S) : Khachin et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1177 days.

Signed and Sealed this

Sixteenth Day of November, 2010

David J. Kappos
*Director of the United States Patent and Trademark Office*